(12) United States Patent
Steinhauser et al.

(10) Patent No.: US 9,427,198 B2
(45) Date of Patent: Aug. 30, 2016

(54) LIVE 3D X-RAY VIEWING

(75) Inventors: Heidrun Steinhauser, Eindhoven (NL);
Michael John Murdoch, Waalre (NL);
Peter Prinsen, Eindhoven (NL)

(73) Assignee: KONINKLIJKE PHILIPS N.V.,
Eindhoven (NL)

( * ) Notice: Subject to any disclaimer, the term of this patent is extended or adjusted under 35 U.S.C. 154(b) by 180 days.

(21) Appl. No.: 14/343,432

(22) PCT Filed: Sep. 13, 2012

(86) PCT No.: PCT/IB2012/054759
§ 371 (c)(1),
(2), (4) Date: Apr. 15, 2014

(87) PCT Pub. No.: WO2013/038355
PCT Pub. Date: Mar. 21, 2013

(65) Prior Publication Data
US 2015/0146843 A1    May 28, 2015

Related U.S. Application Data

(60) Provisional application No. 61/535,506, filed on Sep. 16, 2011.

(51) Int. Cl.
*A61B 6/02* (2006.01)
*A61B 6/00* (2006.01)
*A61B 6/03* (2006.01)
(Continued)

(52) U.S. Cl.
CPC .............. *A61B 6/466* (2013.01); *A61B 6/022* (2013.01); *A61B 6/035* (2013.01); *A61B 6/4021* (2013.01); *A61B 6/4028* (2013.01); *A61B 6/4441* (2013.01); *A61B 6/46* (2013.01); *A61B 6/469* (2013.01); *A61B 6/545* (2013.01); *A61B 6/12* (2013.01); *A61B 6/467* (2013.01); *A61B 6/589* (2013.01); *A61B 2017/00216* (2013.01); *A61B 2090/368* (2016.02)

(58) Field of Classification Search
CPC .......... A61B 6/02; A61B 6/022; A61B 6/54; A61B 6/541; A61B 6/545; A61B 6/547; A61B 6/542; H04N 13/0221; H04N 13/0207; H04N 13/0246; H04N 13/0253; H04N 13/0055; G01N 23/04; H05G 1/60; A61N 5/1048; A61N 5/1049
USPC .............................. 378/41, 62, 95, 98.2, 205
See application file for complete search history.

(56) References Cited

U.S. PATENT DOCUMENTS

| 4,544,949 A | 10/1985 | Kurihara |
| 5,073,914 A | 12/1991 | Asahina et al. |
| 5,233,639 A | 8/1993 | Marks |

(Continued)

FOREIGN PATENT DOCUMENTS

| DE | 463914 | 8/1928 |
| DE | 501802 | 7/1930 |

(Continued)

*Primary Examiner* — Jurie Yun

(57) ABSTRACT

System for live 3D x-ray viewing comprising an x-ray source, an x-ray detector, a processing unit, a monitor and means for detecting viewer's eyes, wherein the x-ray source and the x-ray detector are arranged at a movable C-arm. The x-ray source comprises two focal spots, wherein a separation of the two focal spots is adjustable so that the image acquisition angle between the two focal spots matches the viewing angle between the two eyes.

17 Claims, 4 Drawing Sheets

(51) Int. Cl.
    *A61B 6/12*     (2006.01)
    *A61B 17/00*     (2006.01)

(56) References Cited

U.S. PATENT DOCUMENTS

| | | | |
|---|---|---|---|
| 5,583,345 A | 12/1996 | Kohgami et al. | |
| 5,777,720 A * | 7/1998 | Shapiro | G02B 27/0093 348/E13.022 |
| 6,459,446 B1 * | 10/2002 | Harman | A61B 3/113 348/42 |
| 2006/0227936 A1 | 10/2006 | Dong et al. | |
| 2008/0031411 A1 | 2/2008 | Klingenbeck-Regn | |
| 2009/0238334 A1 | 9/2009 | Brahme et al. | |
| 2010/0040196 A1 | 2/2010 | Zhang et al. | |
| 2010/0110368 A1 | 5/2010 | Chaum | |

FOREIGN PATENT DOCUMENTS

| | | |
|---|---|---|
| DE | 102009010263 | 9/2010 |
| JP | 2005168601 | 6/2005 |

* cited by examiner

LIVE 3D X-RAY VIEWING

CROSS-REFERENCE TO PRIOR APPLICATIONS

This application is the U.S. National Phase application under 35 U.S.C. §371 of International Application Serial No. PCT/IB2012/054759, filed on Sep. 13, 2012, which claims the benefit of U.S. Application Ser. No. 61/535,506, filed on Sep. 16, 2011. These applications are hereby incorporated by reference herein.

FIELD OF THE INVENTION

The invention relates to 3D x-ray imaging. In particular, the invention relates to a system and method for live 3D x-ray viewing. Further, the invention relates to a computer program that implements the method.

BACKGROUND OF THE INVENTION

A known possibility of achieving a 3D volume image is shown in FIG. 1. The system 100 in FIG. 1 comprises a C-arm 2 with an x-ray source 3 and an x-ray detector 4, a monitor 5, and a table 6. The C-arm 2, i.e. one focal spot 8 of the x-ray source 3 together with the x-ray detector 4, rotates around the object of interest (indicated by the curved arrows) and a series of 2D images from different angles are acquired. Reference sign 10 denotes an x-ray beam fan emitted from the focal spot 8 at the anode of the x-ray source 3, and detected by the x-ray detector 4. Subsequently, a 3D reconstruction provides a 3D volume image. However, such a 3D image may not be provided in real-time.

US 2010/0040196 A1 discloses an x-ray generator for achieving a stereoscopic imaging effect and an x-ray device using the x-ray generator as the x-ray source. The x-ray generator with tube can emit x-rays alternately from two positions the space of which conforms to the requirements for achieving stereoscopic imaging effect of the human beings.

However, 3D stereo viewing can cause fatigue and headache due to a variety of cases, including an incorrect or unnatural perspective, the vergence/accommodation conflict, visual artifacts like flicker or resolution loss, and wearing 3D glasses. For example, a discomfort may be caused by a mismatch between the distance to the plane (screen) at which the eyes are focused and the distance to the point at which they converge.

SUMMARY OF THE INVENTION

X-ray stereo imaging can be used for two main purposes: viewing and extraction of positional/directional information. For information extraction (e.g. catheter tracking or registration), it is favorable to have a large distance between the two X-ray spots, which allows good resolution of depth. For 3D stereo viewing, which can give depth information to the viewer in an intuitive way (ease of use), it is important to provide optimum 3D viewing comfort to prevent fatigue.

It can be seen as an objective of the invention to provide a system and method for live 3D x-ray viewing with improved viewing comfort.

This is achieved by the subject matter of each of the independent claims. Further embodiments of the invention are described in the respective dependent claims.

The basic idea of the invention is that the distance between the two X-ray focal spots should match the actual 3D viewing conditions so that correct 3D perspective is given to the viewer's eyes, resulting in improved viewing comfort.

In other words, before starting and/or during live 3D stereo imaging, the distance between the two X-ray stereo focal spots should be adjusted to match the acquisition angle to the viewing angle and thus to give correct 3D perspective to the viewer's eyes to optimize viewing comfort and to prevent fatigue.

Generally, a system for live 3D x-ray viewing in accordance with an aspect of the invention comprises an x-ray source, an x-ray detector, a processing unit, a monitor, and means for detecting eyes of a viewer, wherein the x-ray source and the x-ray detector are arranged on a movable C-arm. The x-ray source comprises two focal spots whose separation is adjustable. Two focal spots may be realized by two cathodes which are movable with respect to each other or by only one cathode with an electrical, magnetic or mechanical deviation of the radiation onto the anode.

The processing unit is adapted to calculate the separation of the two focal spots on the basis of the distance between an object of interest and the two focal spots, the distance between the monitor and the eyes of the viewer, and the separation between the two eyes, and is adapted to provide a command for adjusting the separation of the two focal spots corresponding to the calculated separation.

It is noted that the processing means may be realized by only one processor performing all the aspects of the invention, or by a group or plurality of processors, for example a system processor for controlling the x-ray imaging and processing the x-ray image data, a separate processor specialized in a calculation of the separation, and a further processor for controlling a monitor for visualizing the result.

The 3D visualization may be realized on a monitor with an autostereoscopic display, such as lenticular or barrier-screen displays, or by a combination of a monitor and 3D glasses based on corresponding techniques, for example using means for separating the image for the right eye from the image for the left eye by a shutter technique, colour coding or polarization. It is noted that the term '3D glasses' includes not only complete glasses with earpieces, but also additional elements, for example clip-on elements, for use with regular glasses or lead X-ray protection glasses or anti blood splash glasses.

It will be understood that the processing unit is connected with both the x-ray source and the x-ray detector as well as with the monitor. Furthermore, the distance between the x-ray source and an object of interest positioned between the x-ray source and the x-ray detector, as well as the distance between two lenses of the 3D glasses, i.e. between approximately the centres of the lenses, or between the eyes of a person utilizing the system, can be assumed as known. An average value of the latter distance may be the average eye separation of 6.5 cm. It is also possible to measure these distances once and to input the respective values before starting to use the system.

By the means for detecting the position of the eyes of a viewer, the distance between the monitor and the eyes may be determined, i.e. for example the viewer's eyes positions with respect to the displayed 3D object. For example, a wearable element like trackable glasses may be used. Trackable glasses could be realized by putting trackable LEDs or reflectors on the glasses.

According to another embodiment of the invention, the system further comprises means for adjusting the height of the image on the monitor in relation to the height of the eyes of the viewer. Thus, the 3D image height position may be matched to the viewer's eyes height, to avoid a deviation of the actual viewing direction from the optimal viewing direction which is perpendicular to the plane of the mounted monitor. Accordingly, the optimal viewing direction is horizontal when the screen of the monitor is vertically arranged.

According to a further embodiment of the invention, the system further comprises means for automatically detecting the position and orientation of the eyes, i.e. means for tracking the position and orientation of the eyes. The processing unit may further be adapted to control movements of the C-arm so that the orientation of the C-arm corresponds to the orientation of the eyes of the viewer. In case of the utilization of 3D glasses, the means for detecting the position and/or orientation of the eyes of a viewer may be positioned at the 3D glasses, so that the distance between the screen of the monitor and the eyes is the sum of the determined distance between the screen and the 3D glasses and a constant value representing the distance between the 3D glasses and the eyes of the viewer.

Additionally, the system according to the invention may further comprise means for triggering the controlling of the movements of the C-arm, to temporarily synchronize the C-arm to slight head movements of the viewer around the displayed 3D object to provide even more natural 3D stereo viewing.

According to another embodiment of the invention, the processing unit of the system is further adapted to vary the disparity, i.e. the position of the image for the right eye on the monitor with respect to the image for the left eye, and vice versa. This allows the object of interest to be displayed with minimal disparity, and thus viewed with maximal sharpness.

According to a further aspect of the invention, a method for live 3D x-ray viewing is provided, wherein the method comprises the steps of calculating the separation of two focal spots of an x-ray source on the basis of the distance between an object of interest and the two focal spots, the distance between the monitor and the 3D glasses, i.e. the eyes of a viewer, and the distance between the two lenses of the 3D glasses, i.e. the separation of the eyes, adjusting the separation of the two focal spots according to the calculated separation, generating an x-ray image on the basis of a radiation from one of the two focal spots, generating an x-ray image on the basis of a radiation from the other one of the two focal spots, visualizing both images simultaneously on a monitor, viewable for example with 3D glasses.

According to another embodiment of the invention, the method further comprises the steps of receiving an input related to the height of the image, and adjusting the height of the images relative to the height of the 3D glasses.

According to yet another embodiment of the invention, the method further comprises the steps of receiving an input related to the disparity, i.e., the position of the images with respect to each other, i.e. the overlap of the images, and adjusting the disparity of the images.

According to a further embodiment of the invention, the method further comprises the steps of determining a change of the orientation of the 3D glasses, and moving the C-arm corresponding to the change of the orientation of the 3D glasses. The determination of a change of the orientation of the 3D glasses may be performed automatically. However, the moving of the C-arm may also be controlled manually.

It is noted, that an input may be provided by manual input means like a keyboard, a switch or other kinds of buttons, or may be provided by means of receiving acoustic commands, for example voice commands.

Matching the displayed 3D image height position to the eye height and giving the possibility to temporarily move the C-arm with slight head movements around the displayed 3D object can make the experience even more intuitive and natural.

According to a further aspect of the invention, a computer program is provided which, when executed on a processing unit of a system as described above, causes the system to perform the steps of the method as also described above.

A corresponding computer program is preferably loaded into a work memory of a data processor. The data processor or processing unit is thus equipped to carry out the method of the invention. Further, the invention relates to a computer-readable medium such as a CD-ROM on which the computer program may be stored. However, the computer program may also be presented over a network like the World Wide Web and can be downloaded into the working memory of the data processor from such a network.

It has to be noted that embodiments of the invention are described with reference to different subject-matters. In particular, some embodiments are described with reference to method type claims whereas other embodiments are described with reference to apparatus type claims (system). However, a person skilled in the art will gather from the above and the following description that unless otherwise noted in addition to any combination of features belonging to one type of subject-matter also any combination between features relating to different subject-matters is considered to be disclosed with this application.

The aspects defined above and further aspects, features and advantages of the present invention can also be derived from the examples of the embodiments to be described hereinafter and are explained with reference to examples of embodiments also shown in the figures, but to which the invention is not limited.

BRIEF DESCRIPTION OF THE DRAWINGS

It is noted that the illustration in the drawings is only schematic and not to scale. In different figures, similar elements are provided with the same reference signs.

DETAILED DESCRIPTION OF EMBODIMENTS

Figure 1:
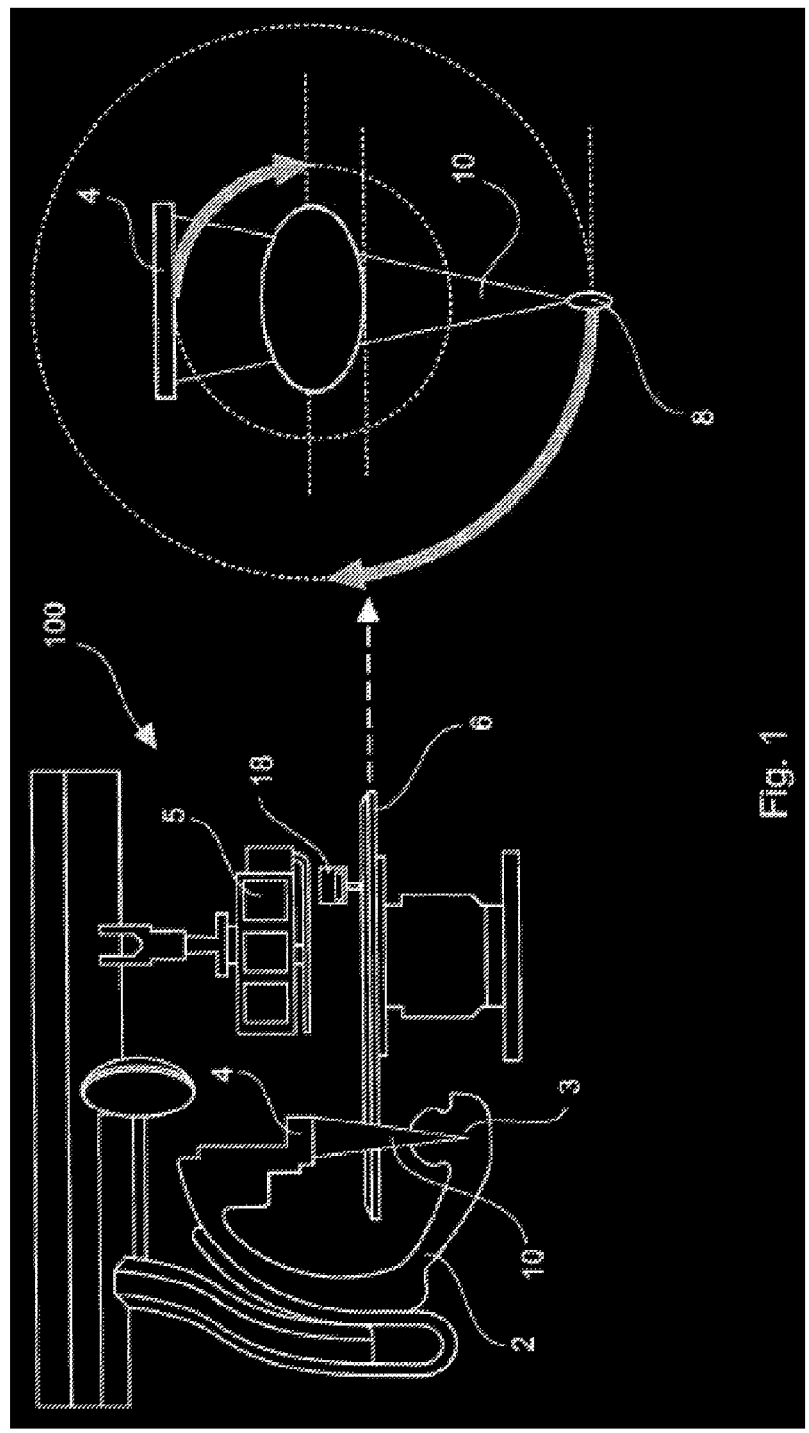
FIG. 1 is an illustration of an x-ray system for 3D volume imaging.
Figure 2:
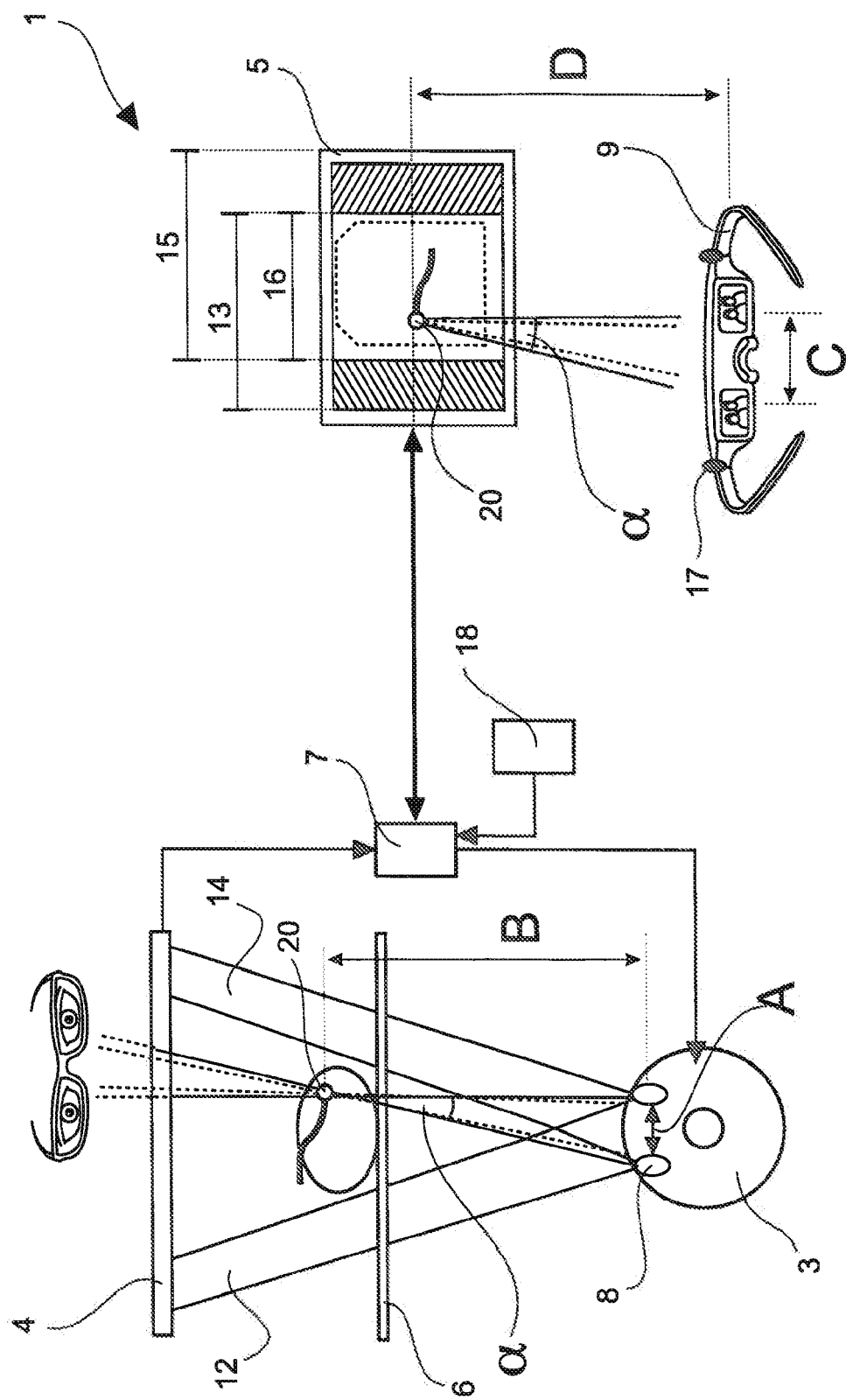
FIG. 2 is an illustration of a system for live 3D x-ray viewing according to the invention.

FIG. 2 shows a system 1 for live 3D x-ray viewing according to the invention. It will be understood that the system 1 is similar to the system 100 shown in FIG. 1, in that the system 1 comprises a C-arm 2 with an x-ray source 3 and an x-ray detector 4, a monitor 5 and a table 6. The system 1 differs from the system 100 in that the x-ray source 3 includes two focal spots 8 instead of only one. Further shown in FIG. 2 is a processing unit 7, an input device 18 and 3D glasses 9 with trackable elements 17.

To achieve a live 3D x-ray viewing in accordance with the invention, trackable LEDs or reflectors 17 may be arranged on the 3D glasses 9 and for example an average eye separation C may be used or the viewer's interpupillary distance may be measured (or eye tracking may be used). Additionally, the live 3D stereo acquisition/viewing conditions according to the viewer's head position may be adjusted with respect to the screen of the monitor 5.

In particular, an improved X-ray 3D stereo viewing comfort is achieved by adjusting the acquisition angle (defined by an object of interest (e.g. a catheter tip) and the two focal spots) to the viewing angle (defined by the displayed object and the eyes).

As indicated in FIG. 2, the viewing distance D (which depends on the application and the actual clinical suite) is determined. Based on the measured eye separation C, an angle α can be calculated, wherein a reasonable approximation is to use an average interpupillary distance to calculate the visual angle. For optimal viewing conditions, this angle α should be the same for the radiations from the two focal spots 8 which are directed to an object of interest 20. Based on the angle α and the distance B between the two focal spots 8 and the object of interest 20, the separation A between the two focal spots can be determined. Subsequently, the focal spot separation A can be adjusted to match the acquisition angle to the viewing angle. A user may select the object of interest (20) for example by a touch-screen, a mouse, etc. Furthermore, the object of interest, assuming it is a catheter, may be automatically detected, based for example on its edge contrast, or pattern-matching.

Deviations from exact matching may be preferred in some cases. For example, a smaller angle may provide more visual comfort, whereas a larger angle may be preferred to exaggerate the depth (for more precision, at the expense of comfort). These deviations could be specified as a scale factor on the general match, and may consistently be applied as the viewer's head moves.

If, for example, the distance between the x-ray source and the object of interest is 1 m, the distance of the eyes from the monitor is 2 m, and the distance between the eyes is 6.5 cm, the separation between the two focal spots should be adjusted to 3.25 cm.

It should be noted that the 3D object of interest (e.g. catheter tip) is ideally presented with zero disparity on the screen (projected on the screen plane), so that focusing of the eyes on the screen means also focusing on the displayed 3D object, which improves the 3D viewing comfort.

Figure 3:
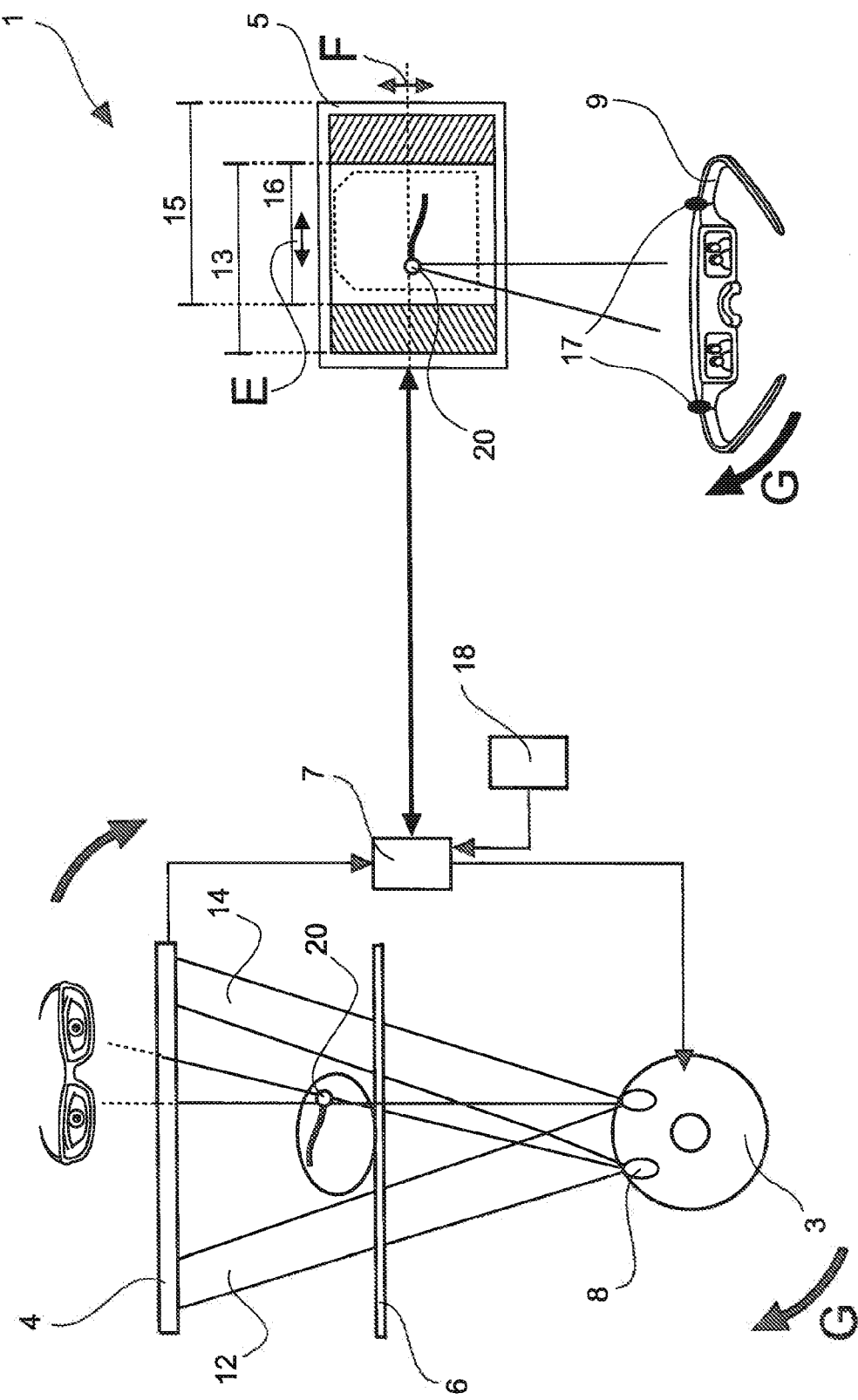
FIG. 3 is a further illustration of a system for live 3D x-ray viewing according to the invention.

In FIG. 3, aspects of adjustments of the live 3D x-ray viewing are indicated.

A first kind of adjustment may be provided by shifting the displayed image 13 with respect to the displayed image 15, indicated by double arrow E (causing an incomplete overlap 16 between the two images) so that the depth position of the object can be changed, i.e. the apparent position of the object with respect to the plane of the screen.

A second kind of adjustment may be that the object might be displayed with some magnification (also related to screen size).

A third kind of adjustment may be a change of the height of the image (as indicated by arrow F). For example, a display may be used with a screen height larger than the 3D stereo image height, so that the height position of the displayed 3D image may be shifted according to the viewer's eye height for optimal viewing. Alternatively, the height of the monitor may be changed, i.e. the monitor may be shifted upwards or downwards.

A fourth kind of adjustment may be to change the perspective relative to the object of interest (as indicated by arrows G). During a difficult 3D task, such as pulling a wire through the eye of a needle, a person is used to adapting the orientation of the object (needle) with respect to his/her head for an improved perspective. The more natural the live 3D x-ray image experiences, the more the viewer will tend to turn his/her head around the visualized 3D object for an improved perspective.

The change of the perspective may be triggered by any kind of input also including voice control. After calling for example "sync", the C-arm follows (in sync) slight movements of the viewer's head around the displayed object: After calling for example "stop", the synchronization stops and the viewer can return to a more comfortable body posture and continue his work with the new perspective.

It is noted that the synchronized C-arm ideally rotates around the object of interest, for example a catheter tip which is visualized at on-screen depth with zero disparity. Thus, the object of interest is centered with respect to the C-arm, during a conventional 3D scan. By way of using a same configuration, it can be ensured that the synchronized C-arm moves in a natural way.

Figure 4:
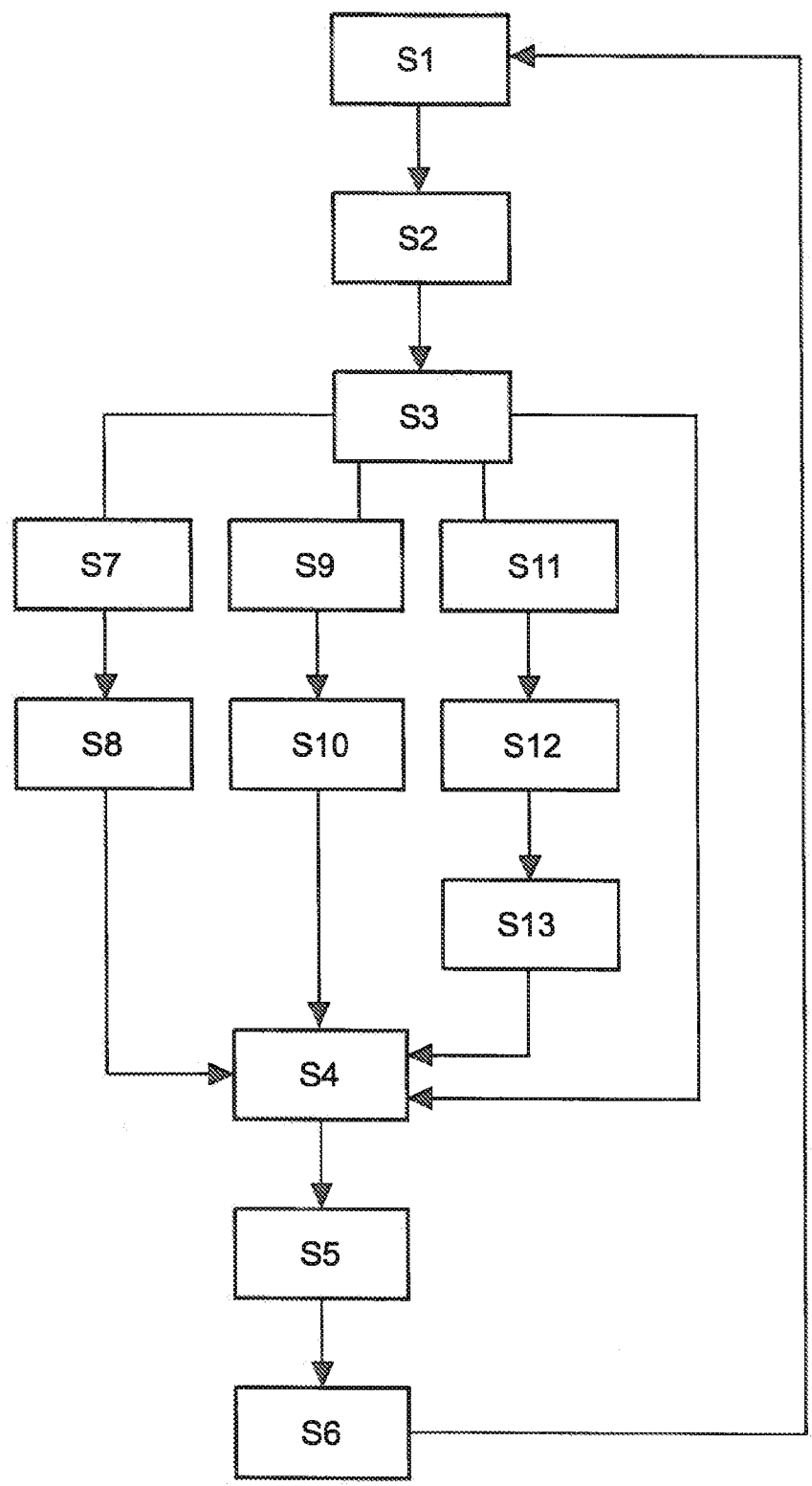
FIG. 4 is a flowchart illustrating steps of a method according to the invention.

The flowchart in FIG. 4 illustrates the principle of the steps performed in accordance with the invention. It will be understood that the steps described are major steps, wherein these major steps might be differentiated or divided into several sub-steps. Furthermore, there might be also sub-steps between these major steps. Therefore, a sub-step is only mentioned if this step may be important for the understanding of the principles of the method according to the invention.

In step S1, the position of the viewer's eyes is determined, especially the distance of the eyes from the monitor.

In step S2, the separation of the focal spots of the x-ray source is calculated, as described above.

In step S3, the actual separation of the focal spots is adjusted.

In step S4, a first image, for example for the right eye, is generated by means of a radiation coming from one of the two focal spots.

In step S5, a second image, for example for the left eye, is generated by means of a radiation coming from the other one of the two focal spots.

In step S6, both images are visualized on the 3D monitor with visual disparity to allow an impression of a 3D image when viewed.

Instead of step S4 directly following step S3, three alternatives may be performed, as indicated in FIG. 4.

As a first alternative, an input is received in step S7, causing the adjustment of the height of the images relative to the height of the viewer's eyes in step S8. In case not only the distance but also the height of the eyes relative to the screen of the monitor is automatically determined, the adjustment of the height of images may also be performed automatically.

As a second alternative, an input is received in step S9, causing the adjustment of the disparity of the images, thus changing the depth position of the object in the 3D image.

As a third alternative, an input is received in step S11, triggering a determination of a movement (change of orientation and position) of the viewer's eyes in step S12, followed by a movement of the C-arm corresponding to the determined movement of the 3D glasses.

While the invention has been illustrated and described in detail in the drawings and afore-going description, such illustrations and descriptions are to be considered illustrative or exemplary and not restrictive, the invention is not limited to the disclosed embodiments.

Other variations to the disclosed embodiments can be understood and effected by those skilled in the art in practising the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims.

The mere fact that certain measures are recited in mutually different dependent claims does not indicate that a combination of these measures can not be used to advantage. The computer program may be stored/distributed on a suitable medium such as an optical storage medium or a solid-state medium supplied together with or as a part of another hardware, but may also be distributed in other forms, such as via the Internet or other wired or wireless telecommunication systems. Any reference signs in the claims should not be construed as limiting the scope.

LIST OF REFERENCE SIGNS 1 system according to invention
100 system according to state of the art
2 C-arm
3 x-ray source
4 x-ray detector
5 monitor
6 patient table
7 processing unit
8 focal spot
9 3D glasses
10 x-ray beam
12 x-ray beam for left eye
13 image for right eye
14 x-ray beam for right eye
15 image for left eye
16 overlap of images
17 means for detecting the position of the 3D glasses
18 input means
20 object of interest
A separation of two focal spots
B distance between object of interest and focal spots
C distance between eyes of a viewer
D distance between monitor and 3D glasses
E change of overlap
F change of image height
G change of orientation of 3D glasses
α viewing angle/acquisition angle

The invention claimed is:

1. A system for live 3D x-ray viewing, the system comprising:
    an x-ray source,
    an x-ray detector,
    a processing unit,
    a monitor and
    a position detector that detects a position of eyes of a viewer and determines the distance between the monitor and the eyes of the viewer, wherein:
    the x-ray source and the x-ray detector are arranged on a C-arm,
    the x-ray source comprises two focal spots,
    a separation of the two focal spots is adjustable,
    the processing unit is adapted to calculate the separation of the two focal spots on the basis of the distance between an object of interest and the focal spots, the distance between the monitor and the eyes of the viewer, and the distance between the eyes of the viewer, and
    the processing unit is adapted to provide a command for adjusting the separation of the two focal spots corresponding to the calculated separation.

2. The system of claim 1, further comprising 3D glasses.

3. The system of claim 1, further comprising an image adjuster that adjusts the height of an image at the monitor in relation to the height of the eyes.

4. The system of claim 1, further comprising:
    an orientation detector that automatically detects the orientation of the eyes, wherein
    the processing unit is further adapted to control movements of the C-arm so that the orientation of the x-ray source and the x-ray detector corresponds to the orientation of the eyes.

5. The system of claim 4, further comprising a triggering device that triggers the controlling of the movements of the C-arm.

6. The system of claim 1, wherein the processing unit is further adapted to vary the overlap region of an image for the right eye and an image for the left eye on the monitor.

7. The system of claim 1, wherein the processing unit:
    determines a viewing angle defined by an image, displayed on the monitor, of the object of interest and the viewer's eyes; and
    adjusts acquisition angles, defined by the object of interest and the two focal spots, for acquiring the two x-ray images, corresponding respectively to the two focal spots, based on the determined viewing angle.

8. The system of claim 1, wherein the processing unit automatically selects the object of interest based on its edge contrast or based on pattern matching.

9. The system of claim 1, wherein the processing unit:
    determines the orientation of the viewer's head with respect to the object of interest; and
    changing the orientation of an image, displayed on the monitor, of the object of interest with respect to the viewer's head based on the determined orientation.

10. A method for live 3D x-ray viewing, the method comprising:
    calculating the separation of two focal spots of an x-ray source, on the basis of the distance between an object of interest and the focal spots, the distance between a monitor and eyes of a viewer, and the distance between the eyes of the viewer,
    adjusting the separation according to the calculated separation,
    generating an x-ray image on the basis of radiation from one of the two focal spots,
    generating an x-ray image on the basis of radiation from the other one of the two focal spots,
    visualizing both images simultaneously on a monitor.

11. The method of claim 10, further comprising:
    receiving an input by an input device, and
    adjusting the height of the images relative to the height of the eyes.

12. The method of claim 10, further comprising:
    receiving an input by an input device, and
    adjusting an overlap of the images.

13. The method of claim 10, further comprising:
    determining a change of the orientation of the eyes, and
    moving a C-arm corresponding to the change of the orientation of the eyes.

14. A non-transitory computer-readable medium storing instructions that when executed by a computer perform the method defined by claim 10.

15. The method of claim 10, further comprising:
    detecting a viewing angle defined by an image, displayed on the monitor, of the object of interest and the viewer's eyes; and adjusting acquisition angles, defined by the object of interest and the two focal spots, for acquiring the two x-ray images, corresponding respectively to the two focal spots, based on the detected viewing angle.

16. The method of claim 10, further comprising automatically selecting the object of interest based on its edge contrast or based on pattern matching.

17. The method of claim 10, further comprising:
detecting the orientation of the viewer's head with respect to the object of interest; and
changing the orientation of an image, displayed on the monitor, of the object of interest with respect to the viewer's head based on the detected orientation.

* * * * *